US006190693B1

(12) United States Patent
Kafrissen et al.

(10) Patent No.: US 6,190,693 B1
(45) Date of Patent: Feb. 20, 2001

(54) PHARMACEUTICAL METHODS OF DELIVERING FOLIC ACID

(75) Inventors: Michael E. Kafrissen, Gladstone, NJ (US); Godfrey Oakley, Atlanta, GA (US)

(73) Assignee: Ortho-McNeil Pharamceutical, Inc., Raritan, NJ (US)

( * ) Notice: Under 35 U.S.C. 154(b), the term of this patent shall be extended for 0 days.

(21) Appl. No.: 09/292,027

(22) Filed: Apr. 16, 1999

Related U.S. Application Data

(60) Provisional application No. 60/082,068, filed on Apr. 17, 1998.

(51) Int. Cl.[7] ................................ A61K 9/48; A61K 9/20
(52) U.S. Cl. ........................................... 424/451; 424/464
(58) Field of Search ....................................... 424/451, 464

(56) References Cited

FOREIGN PATENT DOCUMENTS

| 2131292 | 12/1982 | (GB) . |
| 2 131 292 | 6/1984 | (GB) . |
| WO 88/04927 | 12/1987 | (WO) . |
| WO 98/04248 | 7/1997 | (WO) . |

OTHER PUBLICATIONS

Butterworth, C.E., et al., JAMA (Jan. 1992) 267(4):528–533.
Butterworth, C.E., et al., Am. J. Obstetrics and Gynecology (Aug. 1991) 166:803–809.
Potischman, N. and Brinton, L.A., Cancer Causes and Control (Jul. 1995) 7:113–126.
Boushey, C.J., et al., JAMA (Aug. 1995) 274:1049–1057.
Landgren, F., et al., J. Intern. Med. (Nov. 1994) 237:381–388.
Guttormsen, A.B., et al., J. Clin. Invest. (Nov. 1996) 98:2174–2183.
Gould, P.L., Int'l. J. Pharmaceutics (May 1986) 33:201–217.
Sturdee, D.W., Brit. J. of Obstetrics and Gynecology (Oct. 1997) 104:1109–1115.
Nielsen, M., et al., J. Med. Chem. (Mar. 1988) 32:727–734.
Rhode, B.M., et al., J. of the Am. College of Nutrition (Jun. 1983) 2:221–230.
Butterworth, C.E., et al., Am. J. of Clinical Nutrition (Jan. 1982) 73–82.
Whitehead, N., et al., JAMA (Dec. 1973) 226(12):1421–1424.

*Primary Examiner*—Carlos A. Azpuru
(74) *Attorney, Agent, or Firm*—Alan J. Morrison

(57) ABSTRACT

This invention provides folic acid-containing pharmaceutical compositions comprising either an oral contraceptive or a hormone replacement composition. This invention also provides methods of administering folic acid to a subject using the instant pharmaceutical compositions. Finally, this invention provides a drug delivery system useful for administering the instant pharmaceutical compositions.

8 Claims, No Drawings

PHARMACEUTICAL METHODS OF DELIVERING FOLIC ACID

This application claims benefit of Provisional No. 60/082,068, filed Apr. 17, 1998.

Throughout this application, various publications are cited. The disclosure of these publications is hereby incorporated by reference into this application to describe more fully the state of the art to which this invention pertains.

FIELD OF THE INVENTION

This invention relates to compositions and methods for delivering folic acid to subjects afflicted with, or at an increased risk of becoming afflicted with, a folic acid-treatable disorder. The folic acid is incorporated into a chronically administered pharmaceutical composition intended for treating or preventing a condition different than the folic acid-treatable disorder.

BACKGROUND OF THE INVENTION

Folic Acid Generally

Folic acid is a vitamin. It plays a crucial role in DNA synthesis, and in hematopoiesis (although the details of this role remain undefined). Folic acid is involved, for example, in single carbon transfers (such as those required for purine and pyrimidine metabolism), and in the re-methylation of homocysteine to methionine.

Folic acid is available, primarily as the polyglutamate, from dietary sources such as whole grains, mushrooms, vegetables, red meat, fish and legumes. Supplementation, however, is provided in the form of the monoglutamate (pteroglutamic acid). Folic acid is absorbed primarily in the proximal small bowel, is highly protein-bound, and is stored in the liver. Almost no unchanged folic acid appears in the urine under normal circumstances, unless excess is provided.

Minimum requirements of folic acid are in the range of 50 $\mu$g/day, and increase 3 to 6 times during pregnancy and/or lactation. The U.S. recommended daily allowance for pregnant women is 400 $\mu$g/day, and the average pharmacological replacement dose is between 1 and 5 mg/day. Most prenatal vitamins contain 1 mg of folic acid.

The total body store of folic acid is about 5 mg. When a folic acid-deficient patient is treated, reversal of the deficiency begins rapidly (reticulocytosis within 4 days) and resolves within 2 months. If folic acid is administered at a rate of only 50 $\mu$g day, assuming no dietary or other intake, signs of folic acid deficiency are manifest after an approximately 3 month lag time. In cases of increased bodily folic acid requirements, such as pregnancy or lactation, this time frame is shortened to 2 to 4 weeks. Fortunately, folic acid supplementation in otherwise healthy young women who have such increased folic acid needs is an accepted practice.

Folic acid has not been reported to cause adverse effects when administered in reasonable, pharmacological doses. The only reported adverse reaction for folic acid is a decreased level of plasma zinc in the case of prolonged high-dose administration.

Oral Contraceptives and Folic Acid

In pregnant women, correction of low folic acid levels takes at least two months, and reserves can last as little as a few weeks. According to a public health service recommendation, all women who can become pregnant should consume 400 $\mu$g/day of folic acid to reduce the risk of birth defects (MMWR Morb Mortal Wkly Rep 1992; 41(RR-14):1–7). Supplementation immediately before discontinuing oral contraceptive use or immediately after positive pregnancy test results may be insufficient to optimally protect the developing fetus.

In addition, multiple studies of women taking oral contraceptives show decreased folic acid levels relative to negative controls. Postulated mechanisms reported for this phenomenon include decreased absorption of polyglutamates, increased excretion of folic acids, increased production of folic acid-binding proteins, and induction of folic acid-dependent hepatic microsomal enzymes.

Decreases of folic acid levels among oral contraceptive users pose an additional risk for such users who become pregnant within three to six months following discontinuation of use.

Disorders and Folic Acid

Numerous disorders can result from insufficient intake of folic acid. Enhanced effects of risk factors for cervical dysplasia (e.g. HPV infection) have been linked to decreased folic acid levels. Sub-optimal body stores of folic acid, as measured by red cell folic acid concentrations, may amplify oncogenic risk. Locally diminished folic acid stores, for example, in cervical tissue, may be a result of oral contraceptive use and are responsible for the dysplastic process. Finally, decreased folic acid levels early in pregnancy are associated with increased birth defects, primarily neural tube defects ("NTD's"). Indeed, randomized control trials of vitamin supplements containing folic acid have shown a dramatic reduction of the incidence of spina bifida and anencephaly.

Administering folic acid can reduce the onset of disorders such as cardiovascular disease and cervical dysplasia. For example, most clinical trials show that high folic acid doses (up to 10 mg/day) have a prophylactic, although not therapeutic, effect against cervical dysplasia (Butterworth, C. E., et al., JAMA (1992) 267(4):528–533; Butterworth C. E., et al., Am J Obstet Gynecol (1992) 166:803–809; Potischman, N. and Brinton, L. A., Cancer Causes and Control (1996) 7:113–126).

As for certain cardiovascular disorders, results from numerous studies indicate that doses of folic acid (1–5 mg/day) reduce elevated levels of homocysteine which can cause such disorders (Boushey, C. J., et al., JAMA (1995) 274:1049–1057); Landgren, F., et al., J Intern Med (1995) 237:381–388). A single study by Guttormsen (Guttormsen, A. B., et al., J Clin Invest (1996) 98:2174–2183) demonstrated that low-dose folic acid supplementation (200 $\mu$g/day) reduces elevated plasma homocysteine levels in patients with intermediate hyperhomocysteinemia (>40 $\mu$mol/L). This reduction is influenced, in part, by the initial causes of hyperhomocysteinemia, i.e., genetic mutation, dietary deficiency and concurrent disease.

SUMMARY OF THE INVENTION

This invention provides a pharmaceutical composition comprising (a) an oral contraceptive for preventing pregnancy in a subject, and (b) folic acid in an amount sufficient to treat or prevent a disorder which (i) afflicts subjects for whom the oral contraceptive is indicated at a higher-than-normal incidence, and (ii) is treatable or preventable by folic acid administration.

This invention also provides a pharmaceutical composition comprising (a) a hormonal replacement composition for treating or preventing a menopausal condition in a subject, and (b) folic acid in an amount sufficient to treat or prevent a disorder which (i) afflicts subjects for whom the hormonal replacement composition is indicated at a higher-than-normal incidence, and (ii) is treatable or preventable by folic acid administration.

This invention further provides a pharmaceutical composition comprising (a) a hormonal replacement composition for treating or preventing a hypogonadal condition in a subject, and (b) folic acid in an amount sufficient to treat or prevent a disorder which (i) afflicts subjects for whom the hormonal replacement composition is indicated at a higher-than-normal incidence, and (ii) is treatable or preventable by folic acid administration.

This invention further provides a method of administering folic acid to a subject for whom an oral contraceptive is indicated for preventing pregnancy, which comprises administering to the subject the instant pharmaceutical composition, wherein the subject is from a population whose members are afflicted with, or predisposed to become afflicted with, a disorder at a higher-than-normal incidence, the disorder being treatable or preventable by folic acid administration.

This invention further provides a method of administering folic acid to a subject for whom a hormonal replacement composition is indicated for treating or preventing a menopausal condition, which comprises administering to the subject the instant pharmaceutical composition, wherein the subject is from a population whose members are afflicted with, or predisposed to become afflicted with, a disorder at a higher-than-normal incidence, the disorder being treatable or preventable by folic acid administration.

This invention further provides a method of administering folic acid to a subject for whom a hormonal replacement composition is indicated for treating or preventing a hypogonadal condition, which comprises administering to the subject the instant pharmaceutical composition, wherein the subject is from a population whose members are afflicted with, or predisposed to become afflicted with, a disorder at a higher-than-normal incidence, the disorder being treatable or preventable by folic acid administration.

Finally, this invention provides a drug delivery system comprising a pharmaceutical package containing a plurality of dosage units, adapted for successive daily administration, wherein each dosage unit comprises at least one of the instant pharmaceutical compositions.

DETAILED DESCRIPTION OF THE INVENTION

Definitions

In this invention, certain terms are used which shall have the meanings set forth as follows.

"Androgen-related compound" ("ARC") shall mean a compound which displays an end organ androgen effect. ARC's are exemplified in the Examples below.

"Chronic administration" shall mean administration which occurs either at regular intervals (e.g., daily oral dosage) or continuously (e.g. transdermal delivery for several days) over at least a single time period (e.g., three weeks). The chronic administration can optionally occur over a plurality of time periods.

"Estrogen-related compound" ("ERC") shall mean a compound which displays an end organ estrogen effect. ERC's are exemplified in the Examples below.

"Folic acid" shall mean the compound having the following structure, where R and R' are both H, as well as pharmaceutically acceptable salts and derivatives thereof:

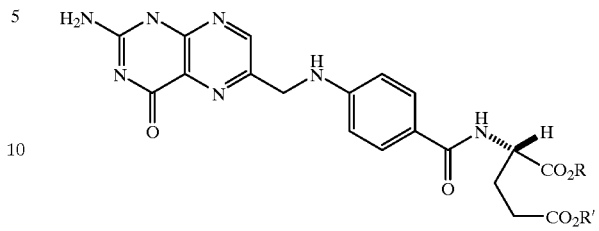

Pharmaceutically acceptable salts are well known in the art and include, without limitation, $Na^+$, $K^+$, $Mg^{++}$ and various amines (Int'l. J. Pharm. (1986) 33:201–217). Pharmaceutically acceptable derivatives are also well known in the art and include, without limitation, esters. Such derivatives are exemplified below.

"Menopausal condition" shall mean a condition that is either a peri-menopausal condition or a post-menopausal condition.

"Menopausal woman" shall mean a woman having an age at which menopause or its onset normally occurs.

"Peri-menopausal condition" shall mean a condition which (i) occurs either during menopausal onset, or prior thereto at a time when menopausal onset normally occurs, and (ii) either is caused by menopausal onset or has a greater than random coincidence therewith. Peri-menopausal conditions include, for example, hot flashes and reduction of bone mass.

"Post-menopausal condition" shall mean a condition which (i) occurs after menopausal onset, and (ii) either is caused by menopause or has a greater than random coincidence therewith. Post-menopausal conditions include, for example, vasomotor symptoms, osteopenia, osteoporosis, cardiovascular disease and cognitive dysfunction.

"Progestin-related compound" ("PRC") shall mean a compound which displays an end organ progestin effect. PRC's are exemplified in the Examples below.

"Subject" shall any animal, such as a primate, mouse, rat, guinea pig or rabbit. In the preferred embodiment, the subject is a human.

EMBODIMENTS OF THE INVENTION

This invention provides a pharmaceutical composition comprising (a) an oral contraceptive for preventing pregnancy in a subject, and (b) folic acid in an amount sufficient to treat or prevent a disorder which (i) afflicts subjects for whom the oral contraceptive is indicated at a higher-than-normal incidence, and (ii) is treatable or preventable by folic acid administration.

This invention also provides a method of administering folic acid to a subject for whom an oral contraceptive is indicated for preventing pregnancy, which comprises administering to the subject the instant pharmaceutical composition, wherein the subject is from a population whose members are afflicted with, or predisposed to become afflicted with, a disorder at a higher-than-normal incidence, the disorder being treatable or preventable by folic acid administration.

Oral contraceptives are widely available commercially, and classifications thereof include, without limitation, progestin only, fixed dose, and phasics. Oral contraceptives routinely contain one or more estrogen-related compounds and progestin-related compounds. Such contraceptives are preferred in this invention and are listed extensively, along with their respective hormone ingredients, in the IPPF Directory of Hormonal Contraceptives. For the purpose of illustration, selected oral contraceptives and their respective hormone ingredients are listed in the Examples below.

In this embodiment, the disorder can be any folic acid-treatable condition with which pregnant women are afflicted, or to which they are predisposed to become afflicted, at a higher-than-normal incidence. In the preferred embodiment, the disorder is selected from the group consisting of a teratogenic disorder, cervical dysplasia, a cervical carcinoma, and a cardiovascular disorder.

This invention also provides a pharmaceutical composition comprising (a) a hormonal replacement composition for treating or preventing a menopausal condition in a subject, and (b) folic acid in an amount sufficient to treat or prevent a disorder which (i) afflicts subjects for whom the hormonal replacement composition is indicated at a higher-than-normal incidence, and (ii) is treatable or preventable by folic acid administration.

This invention further provides a method of administering folic acid to a subject for whom a hormonal replacement composition is indicated for treating or preventing a menopausal condition, which comprises administering to the subject the instant pharmaceutical composition, wherein the subject is from a population whose members are afflicted with, or predisposed to become afflicted with, a disorder at a higher-than-normal incidence, the disorder being treatable or preventable by folic acid administration.

The menopausal condition can be a peri-menopausal condition or, alternatively, a post-menopausal condition. Hormonal replacement compositions are widely available commercially, and routinely contain estrogen-related compounds, progestin-related compounds, androgen-related compounds, and others. Such compositions are preferred in this invention and are listed extensively, along with their respective hormone ingredients, in Sturdee, D. W., et al. (Br J Obstet Gynecol (1997) 104:109–115). By way of example, selected hormone replacement compositions and their respective hormone ingredients are listed in the Examples below.

In this embodiment, the disorder can be any folic acid-treatable condition with which menopausal women are afflicted, or to which they are predisposed to become afflicted, at a higher-than-normal incidence. In the preferred embodiment, the disorder is selected from the group consisting of cervical dysplasia, cervical carcinoma and a cardiovascular disorder.

This invention also provides a pharmaceutical composition comprising (a) a hormonal replacement composition for treating or preventing a hypogonadal condition in a subject, and (b) folic acid in an amount sufficient to treat or prevent a disorder which (i) afflicts subjects for whom the hormonal replacement composition is indicated at a higher-than-normal incidence, and (ii) is treatable or preventable by folic acid administration.

This invention further provides a method of administering folic acid to a subject for whom a hormonal replacement composition is indicated for treating or preventing a hypogonadal condition, which comprises administering to the subject the instant pharmaceutical composition, wherein the subject is from a population whose members are afflicted with, or predisposed to become afflicted with, a disorder at a higher-than-normal incidence, the disorder being treatable or preventable by folic acid administration.

Hormone replacement compositions for hypogonadal conditions routinely contain androgen-related compounds (for male subjects) and estrogen- and progestin-related compounds (for female subjects). Hypogonadal conditions include, by way of example, menopause (with or without reduced libido), Klinefelter's syndrome, and post-orchectomy status. When the subject is female, the disorder can be selected, for example, from the group consisting of a teratogenic disorder, cervical dysplasia, a cervical carcinoma, and a cardiovascular disorder. When the subject is male, the disorder can be, for example, a cardiovascular disorder.

In this invention, administering the instant pharmaceutical compositions can be effected or performed using any of the various methods and delivery systems known to those skilled in the art. The administering can be performed, for example, intravenously, orally, via implant, transmucosally, transdermally, intramuscularly, and subcutaneously. In addition, the instant pharmaceutical compositions ideally contain one or more routinely used pharmaceutically acceptable carriers. Such carriers are well known to those skilled in the art. The following delivery systems, which employ a number of routinely used carriers, are only representative of the many embodiments envisioned for administering the instant composition.

Transdermal delivery systems include patches, gels, tapes and creams, and can contain excipients such as solubilizers, permeation enhancers (e.g., fatty acids, fatty acid esters, fatty alcohols and amino acids), hydrophilic polymers (e.g., polycarbophil and polyvinylpyrrolidone), and adhesives and tackifiers (e.g., polyisobutylenes, silicone-based adhesives, acrylates and polybutene).

The transdermal administration of folic acid can be facilitated by using the following ester form, which is hydrolyzed in vivo:

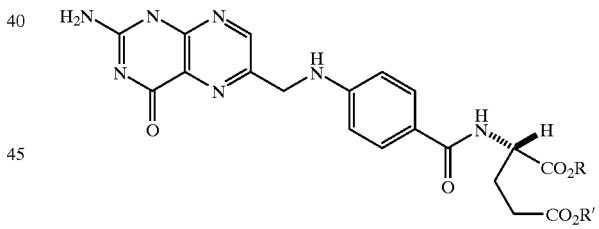

This ester can be a mono-ester (where either R or R'=H) or a di-ester (where neither R or R' is H). By way of example, R and R' can be independently selected from the following groups: lower alkyl from 1–8 carbons (e.g., methyl, ethyl, propyl and butyl); branched lower alkyl from 1–8 carbons (e.g., isopropyl, isobutyl and sec-butyl); cycloalkyl having 3–7 carbons (e.g., cyclopentyl and cyclohexyl); aryl (e.g., phenyl and substituted phenyl having 1–2 substitutients selected from lower alkyl and halo alkoxyl); and arylalkyl, where the alkyl is a straight or branched chain of 1–8 carbons, and aryl is a phenyl or substituted phenyl.

Glycolamide esters (both mono- and di-) can also be used for transdermal folic acid administration. Esters of this type are known to be useful as pro-drugs, and are cleaved rapidly in-vivo (J. Med. Chem. (1989) 32(3):727–34). In glycolamide esters, at least one of R or R' has the structure:

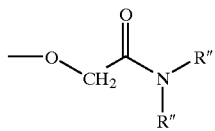

where (i) each R" is independently a lower alkyl (from 1–5 carbons) or, alternatively, (ii) both R" groups form an N-containing, 5–7-membered ring having 4–6 carbons.

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

Methods of determining therapeutically effective doses for administering the instant pharmaceutical composition in humans are known in the art. For example, these effective doses can readily be determined mathematically from the results of animal studies.

In one embodiment of the instant invention, the daily dose of folic acid administered to a subject according to the instant invention is from about 25 μg to about 1 g. Current recommendations in the art for daily folic acid dosages, upon which indication-specific dosages can readily be determined, include, for example: 50 μg/day (minimum effective dose, general population); 200 μg/day (recommended daily allowance, general population); 400 μg/day (women of reproductive age); 800 μg/day (pregnant women); 500 μg/day (lactating women); 4 mg/day (women who have previously delivered a fetus having NTD); 1–5 mg/day (reduction of elevated homocysteine levels); and 200 μg/day (reduction of elevated plasma homocysteine levels in intermediate hyperhomocysteinemia patients).

The instant pharmaceutical compositions can be packaged in the form of pharmaceutical kits or packages in which the daily (or other periodic) dosages are arranged for proper sequential administration. Accordingly, this invention further provides a drug delivery system comprising a pharmaceutical package containing a plurality of dosage units, adapted for successive daily administration, each dosage unit comprising at least one of the instant pharmaceutical compositions.

This drug delivery system can be used to facilitate administering any of the various embodiments of the instant pharmaceutical compositions. In one embodiment, the system contains a plurality of dosages to be taken daily via oral administration (as commonly practiced in the oral contraceptive art). In another embodiment, the system contains a plurality of dosages to be administered weekly via transdermal administration (as commonly practiced in the hormone replacement art), thus providing continuous folic acid delivery.

For added convenience, the instant system can further comprise additional dosage units that contain folic acid, but no other active ingredient. Such delivery system could provide a total of 28 oral dosage units, consistent with normal practice in the art of oral contraception. More specifically, an oral contraceptive delivery system could provide 21 daily dosage units, each comprising folic acid and oral contraceptive, and 7 additional dosage units comprising only folic acid and a suitable carrier. This type of system is consistent with the beneficial practice of daily, uninterrupted administration widely used with oral contraceptives.

This invention will be better understood by reference to the Examples which follow, but those skilled in the art will readily appreciate that the information detailed is only illustrative of the invention as described more fully in the claims which follow thereafter.

EXAMPLE 1

Estrogen-Related Compounds

17-β-estradiol
Conjugated estrogens (including estrone sulfate, equilin, and 17-α-dihydroequilin)
Esterified estrogens
Estradiol
Estradiol valerate
Estriol
Estrone
Estrone sulfate
Estropipate
Ethinyl estradiol
Mestranol

EXAMPLE 2

Selective Estrogen Receptor Modulators (SERMS)

Droloxifene
Idoxifene
Levormeloxifene
Raloxifene

EXAMPLE 3

Progestin-Related Compounds
Available World-Wide 17-deacetyl norgestimate
Desogestrel
Ethynodiol diacetate
Levonorgestrel
Medroxyprogesterone acetate
Norethindrone
Norethindrone acetate
Norgestimate
Norgestrel Progesterone Available Outside the U.S.

3-keto desogestrel
Chlormadinone acetate
Cyproterone acetate
Dienogest
Dydrogesterone
Gestodene
Lynestrenol
Megestrol
Norethisterone
Norethisterone acetate
Norgestrienone
Quingestanol acetate

EXAMPLE 4

Androgen-Related Compounds

Fluoxymesterone
Methyltestosterone
Testosterone
Testosterone enanthate

EXAMPLE 5

Oral Contraceptives

| Brand Name | Manufacturer** | ERC | PRC |
|---|---|---|---|
| DESOGEN | Organon | Ethinyl estradiol | Desogestrel |
| ORTHO CEPT | Ortho McNeil | Ethinyl estradiol | Desogestrel |
| DEMULEN 1/50 | Searle | Ethinyl estradiol | Ethynodiol diacetate |
| ZOVIA 1/35 | Watson | Ethinyl estradiol | Ethynodiol diacetate |
| DEMULEN 1/35 | Searle | Ethinyl estradiol | Ethynodiol diacetate |
| ZOVIA 1/50 | Watson | Ethinyl estradiol | Ethynodiol diacetate |
| LEVLEN | Berlex | Ethinyl estradiol | Levonorgestrel |
| TRI-LEVLEN | Berlex | Ethinyl estradiol | Levonorgestrel |
| LEVORA | Watson | Ethinyl estradiol | Levonorgestrel |
| ALESSE | Wyeth Ayerst | Ethinyl estradiol | Levonorgestrel |
| NORDETTE | Wyeth Ayerst | Ethinyl estradiol | Levonorgestrel |
| TRIPHASIL | Wyeth Ayerst | Ethinyl estradiol | Levonorgestrel |
| OVCON 35 | Apothecon | Ethinyl estradiol | Norethindrone |
| OVCON 50 | Apothecon | Ethinyl estradiol | Norethindrone |
| JENEST | Organon | Ethinyl estradiol | Norethindrone |
| ORTHO NOVUM 7/7/7 | Ortho McNeil | Ethinyl estradiol | Norethindrone |
| ORTHO NOVUM 1/35 | Ortho McNeil | Ethinyl estradiol | Norethindrone |
| ORTHO NOVUM 1/50 | Ortho McNeil | Mestranol | Norethindrone |
| ORTHO NOVUM 10-11 | Ortho McNeil | Ethinyl estradiol | Norethindrone |
| NORETHIN 1/35E | Roberts | Ethinyl estradiol | Norethindrone |
| NORETHIN 1/50M | Roberts | Mestranol | Norethindrone |
| NORETHIN 1/35 | Searle | Ethinyl estradiol | Norethindrone |
| NORETHIN 1/50 | Searle | Mestranol | Norethindrone |
| BREVICON | Searle | Ethinyl estradiol | Norethindrone |
| NORINYL 1+35 | Searle | Ethinyl estradiol | Norethindrone |
| NORINYL 1+50 | Searle | Mestranol | Norethindrone |
| NOR-QD | Searle | | Norethindrone |
| TRI-NORINYL | Searle | Ethinyl estradiol | Norethindrone |
| NELOVA 0.5/35 | Warner Chilcott | Ethinyl estradiol | Norethindrone |
| NELOVA 1/35 | Warner Chilcott | Ethinyl estradiol | Norethindrone |
| NELOVA 1/50 | Warner Chilcott | Mestranol | Norethindrone |
| NELOVA 10/11 | Warner Chilcott | Ethinyl estradiol | Norethindrone |
| NECON 0.5/35 | Watson | Ethinyl estradiol | Norethindrone |
| NECON 1/35 | Watson | Ethinyl estradiol | Norethindrone |
| NECON 1/50 | Watson | Mestranol | Norethindrone |
| NECON 10/11 | Watson | Ethinyl estradiol | Norethindrone |
| ESTROSTEP 21 | Parke Davis | Ethinyl estradiol | Norethindrone acetate |
| ESTROSTEP Fe | Parke Davis | Ethinyl estradiol | Norethindrone acetate |
| LOESTRIN Fe 1.5/30 | Parke Davis | Ethinyl estradiol | Norethindrone acetate |
| LOESTRIN Fe 1/20 | Parke Davis | Ethinyl estradiol | Norethindrone acetate |
| NORLESTRIN 1/50 | Parke Davis | Ethinyl estradiol | Norethindrone acetate |
| NORLESTRIN 2.5/50 | Parke Davis | Ethinyl estradiol | Norethindrone acetate |
| GENORA 1/35 | Watson | Ethinyl estradiol | Norethisterone |
| GENORA 1/50 | Watson | Mestranol | Norethisterone |
| GENORA 0.5/35 | Watson | Ethinyl estradiol | Norethisterone |
| MICRONOR | Ortho McNeil | | Norgestimate |
| ORTHO CYCLEN | Ortho McNeil | Ehinyl estradiol | Norgestimate |
| ORTHO TRI-CYCLEN | Ortho McNeil | Ethinyl estradiol | Norgestimate |
| LO/OVRAL | Wyeth Ayerst | Ethinyl estradiol | Norgestrel |
| OVRAL | Wyeth Ayerst | Ethinyl estradiol | Norgestrel |
| OVRETTE | Wyeth Ayerst | | Norgestrel |

**The manufacturers listed in this and other Examples are fully identified, by address, in Physicians' Desk Reference, 51$^{st}$ Ed. (1997) Medical Economics.

EXAMPLE 6

Hormone Replacement Therapy
Vaginal Estrogen Preparations

| Brand | ERC | Formulation |
|---|---|---|
| PREMARIN | Conj. Estrogens | Cream |
| ORTHO DIENOESTROL | Dienoestrol | Cream |
| OVESTIN | Estriol | Cream |
| ORTHO-GYNEST | Estriol | Pessary |

Hormone Replacement Therapy
Vaginal Estrogen Preparations

| Brand | ERC | Formulation |
|---|---|---|
| TAMPOVAGAN | Stilbestrol | Pessary |
| ESTRING | Estradiol | Vaginal ring |
| VAGIFEM | Estradiol | Vaginal tablet |

EXAMPLE 7

Hormone Replacement Therapy
Transdermal Estrogen Preparations

| Brand | ERC |
|---|---|
| ALORA | Estradiol |
| CLIMARA | Estradiol |
| DERMESTRIL | Estradiol |
| ESTRADERM | Estradiol |
| ESTRADERM TTS or MX | Estradiol |
| EVOREL | Estradiol |
| FEMATRIX | Estradiol |
| FEMPATCH | Estradiol |
| FEMSEVEN | Estradiol |
| MENOREST | Estradiol |
| PROGYNOVA TS | Estradiol |
| VIVELLE | Estradiol |

EXAMPLE 8

Hormone Replacement Therapy
Period-Free Therapy

| Type | Brand | ERC | PRC |
|---|---|---|---|
| Continuous Combined therapy | CLIMESSE | Estradiol | Norethisterone |
| | EVORELCONTI | Estradiol | Norethisterone |
| | KLIOFEM | Estradiol | Norethisterone |
| | PREMIQUE | Conj. Estrogens | Medroxyprogesterone |
| | PREMPRO | Conj. Estrogens | Medroxyprogesterone acetate |
| Gonadomimetic | LIVIAL | | |

EXAMPLE 9

Hormone Replacement Therapy
Estrogen Preparations

| Brand | ERC | Formulation |
|---|---|---|
| ESTROGEL | Estradiol | Gel |
| SANDRENA | Estradiol | Gel |
| ESTRADIOL IMPLANT | Estradiol | Pellet implant |
| PREMARIN | Conjugated estrogens | Tablet |
| ESTRATAB | Esterified estrogens | Tablet |
| ESTRATEST | Esterified estrogens | Tablet |
| ESTRATEST HS | Methyltestosterone | |
| MENEST | Esterified estrogens | Tablet |
| CLIMAGEST | Estradiol | Tablet |
| CLIMAVAL | Estradiol | Tablet |
| ELLESTE SOLO | Estradiol | Tablet |
| ESTRACE | Estradiol | Tablet |
| PROGYNOVA | Estradiol | Tablet |

Hormone Replacement Therapy
Estrogen Preparations

| Brand | ERC | Formulation |
|---|---|---|
| ZUMENON | Estradiol | Tablet |
| HORMONIN | Estradiol, estrone, estriol | Tablet |
| HARMOEN | Estrone | Tablet |
| OGEN | Estropipate | Tablet |
| ORTHO-EST | Estropipate | Tablet |

EXAMPLE 10

Combined Sequential Hormone Replacement Therapy

| Type | Brand | ERC | PRC | Formul. |
|---|---|---|---|---|
| 1/month | PREMIQUE CYCLE | Conj. Estrogens | Medroxy-progesterone | Tablet |
| | PREMPHASE | Conj. Estrogens | Medroxyproges-terone acetate | Tablet |
| | PREMPAK-C | Conj. Estrogens | Norgestrel | Tablet |
| | FEMPAK | Estradiol | Dydrogesterone | Tablet Patch |
| | FEMOSTON | Estradiol | Dydrogesterone | Tablet |
| | CYCLO-PROGYNOVA | Estradiol | Levonorgestrel | Tablet |
| | NUVELLE | Estradiol | Levonorgestrel | Tablet |
| | NUVELLE TS | Estradiol | Levonorgestrel | Patch |
| | CLIMAGEST | Estradiol | Norethisterone | Tablet |
| | ELLESTE DUET | Estradiol | Norethisterone | Tablet |
| | ESTRACOMBI | Estradiol | Norethisterone | Tablet Patches |
| | ESTRAPAK | Estradiol | Norethisterone | Tablet Patches |
| | EVOREL-PAK | Estradiol | Norethisterone | Tablet Patches |
| | EVORELSEQUI | Estradiol | Norethisterone | Tablet Patches |
| | TRISEQUENS | Estradiol, estriol | Norethisterone | Tablet |
| | IMPROVERA | Estrone | Medroxy-progesterone | Tablet |
| | MENOPHASE | Mestranol | Norethisterone | Tablet |
| 1/qtr. | TRIDESTRA | Estradiol | Medroxy-progesterone | Tablet |

EXAMPLE 11

Hormone Replacement Therapy
Progestin-Only Formulations

| Brand | PRC | Formulation |
|---|---|---|
| AMEN | Medroxyprogesterone acetate | Tablet |
| CYCRIN | Medroxyprogesterone acetate | Tablet |
| PROVERA | Medroxyprogesterone acetate | Tablet |
| AYGESTIN | Norethindrone acetate | Tablet |

EXAMPLE 12

| Hormone Replacement Therapy Androgenic Formulations | | |
|---|---|---|
| Brand Name | Manufacturer | Hormone Content |
| HALOTESTIN | Upjohn | Fluoxymesterone Oral |
| ANDROID | ICN | Methyltestosterone Oral |
| ORETON | ICN | Methyltestosterone Oral |
| TESTRED | ICN | Methyltestosterone Oral |
| DEPO-TESTOSTERONE | Upjohn | Testosterone cypionate Injectable |
| DELATESTRYL | BTG Pharmaceuticals | Testosterone enanthate Injectable |
| TESTODERM | Alza | Testosterone, USP Transdermal |

EXAMPLE 13

Formulation For Folic Acid-Containing Oral Contraceptive

Ethinyl Estradiol (to deliver 35 μg)
Norethindrone (to deliver 1.0 mg)
Folic Acid (to deliver 400 μg)
Lactose, NF
Pregelatinized Starch, NF
Magnesium Stearate, NF

What is claimed is:

1. A method of administering folic acid to a subject for whom a hormonal replacement composition is indicated for treating or preventing a menopausal condition, which comprises administering to the subject a pharmaceutical composition, wherein
    (a) the pharmaceutical composition comprises a hormonal replacement composition for treating or preventing a menopausal condition in a subject, and folic acid in an amount sufficient to treat or prevent a disorder which (i) afflicts subjects for whom the hormonal replacement composition is indicated at a higher-than-normal incidence, and (ii) is treatable or preventable by folic acid administration, and
    (b) the subject is from a population whose members are afflicted with, or predisposed to become afflicted with, a disorder at a higher-than-normal incidence, the disorder being treatable or preventable by folic acid administration.

2. The method of claim 1, wherein the menopausal condition is a peri-menopausal condition.

3. The method of claim 1, wherein the menopausal condition is a post-menopausal condition.

4. The method of claim 1, wherein the disorder is selected from the group consisting of cervical dysplasia, a cervical carcinoma, and a cardiovascular disorder.

5. A method of administering folic acid to a subject for whom a hormonal replacement composition is indicated for treating or preventing a hypogonadal condition, which comprises administering to the subject a pharmaceutical composition, wherein
    (a) the pharmaceutical composition comprises a hormonal replacement composition for treating or preventing a hypogonadal condition in a subject, and folic acid in an amount sufficient to treat or prevent a disorder which (i) afflicts subjects for whom the hormonal replacement composition is indicated at a higher-than-normal incidence, and (ii) is treatable or preventable by folic acid administration, and
    (b) the subject is from a population whose members are afflicted with, or predisposed to become afflicted with, a disorder at a higher-than-normal incidence, the disorder being treatable or preventable by folic acid administration.

6. The method of claim 5, wherein the subject is female, and the disorder is selected from the group consisting of a teratogenic disorder, cervical dysplasia, a cervical carcinoma, and a cardiovascular disorder.

7. The method of claim 5, wherein the subject is male, and the disorder is a cardiovascular disorder.

8. A method of administering folic acid to a subject for whom an oral contraceptive is indicated for preventing pregnancy, which comprises administering to the subject a pharmaceutical composition, wherein
    (a) the pharmaceutical composition comprises an oral contraceptive for preventing pregnancy in a subject, and folic acid in an amount sufficient to treat or prevent a teratogenic or cardiovascular disorder which (i) afflicts subjects for whom the oral contraceptive is indicated at a higher-than-normal incidence, and (ii) is treatable or preventable by folic acid administration, and
    (b) the subject is from a population whose members are afflicted with, or predisposed to become afflicted with, a teratogenic or cardiovascular disorder at a higher-than-normal incidence, the disorder being treatable or preventable by folic acid administration.

* * * * *

UNITED STATES PATENT AND TRADEMARK OFFICE
CERTIFICATE OF CORRECTION

PATENT NO.    : 6,190,693 B1
DATED         : February 20, 2001
INVENTOR(S)   : Kafrissen et al.

It is certified that error appears in the above-identified patent and that said Letters Patent is hereby corrected as shown below:

<u>Title page,</u>
Item [73], Assignee: the following should be added as an Assignee:
-- Government of the United States, as represented by the Secretary, Department of Health and Human Services C/O Centers for Disease Control and Prevention, Technology Transfer Office --

Signed and Sealed this

Thirteenth Day of April, 2004

JON W. DUDAS
*Acting Director of the United States Patent and Trademark Office*